Figure 1:
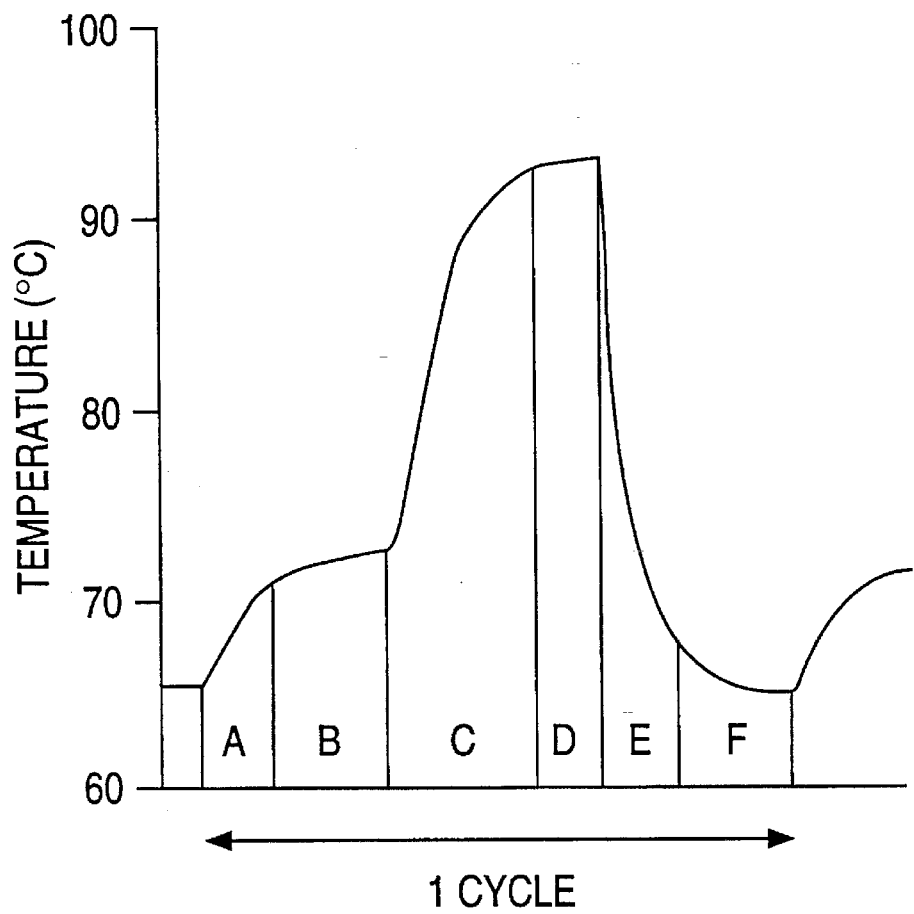

US005552275A

United States Patent [19]
Hui et al.

[11] Patent Number: 5,552,275
[45] Date of Patent: Sep. 3, 1996

[54] HUMAN LEUKOCYTE ANTIGEN TYPING

[75] Inventors: Kam M. Hui, Kent Ridge, Singapore; Jeffrey L. Bidwell, Bristol, United Kingdom

[73] Assignee: National University of Singapore, Singapore

[21] Appl. No.: 200,949

[22] Filed: Feb. 23, 1994

Related U.S. Application Data

[63] Continuation of Ser. No. 116,043, Sep. 1, 1993, abandoned, which is a continuation of Ser. No. 652,072, Feb. 6, 1991, abandoned.

[30] Foreign Application Priority Data

Feb. 6, 1990 [GB] United Kingdom ............... 9002625

[51] Int. Cl.⁶ ............... C12Q 1/68; C12Q 1/48; C21P 19/34
[52] U.S. Cl. ............... 435/6; 435/15; 435/91.2; 435/172.1; 435/810; 935/17; 935/77; 935/78
[58] Field of Search ............... 435/6, 15, 91.2, 435/172.1, 810; 935/17, 77, 78

[56] References Cited

U.S. PATENT DOCUMENTS 4,582,788  4/1986  Erlich ............................ 435/6

FOREIGN PATENT DOCUMENTS

| 0164876 | 12/1985 | European Pat. Off. . |
|---|---|---|
| 0200362 | 12/1986 | European Pat. Off. . |
| 0237362 | 9/1987 | European Pat. Off. . |
| 0317239 | 5/1989 | European Pat. Off. . |
| WO83/03260 | 9/1983 | WIPO . |
| WO89/01050 | 2/1989 | WIPO . |
| WO89/04875 | 6/1989 | WIPO . |
| WO89/07149 | 8/1989 | WIPO . |
| WO90/11547 | 11/1989 | WIPO . |
| WO89/11548 | 11/1989 | WIPO . |
| WO90/04648 | 5/1990 | WIPO . |
| WO90/13668 | 11/1990 | WIPO . |

OTHER PUBLICATIONS

Bidwell et al., "A DNA–RFLP Typing System that Positively Identifies Serologically Well–defined and Ill–defined HLA–DR and DQ Alleles, Including DRw10," *Transplantation*, 45:640–646 (1988).

Wood et al., "HLA–DR Typing of Renal Allograft Patients and Donors by DNA–RFLP:Correlation with Pretransplant Serotyping," *Transplantation Proceedings* 22:2287 (Oct. 1990).

Mytilineos et al., "Comparison of RFLP–DR beta and Serological HLA–DR–typing in 1500 Individuals," *Transplantation* 59:870–873 (Nov. 1990).

Middleton et al., "Discrepancies in serological tissue typing revealed by DNA techniques," *Transplant Int* 1:161–164 (1988).

Clay et al., "PCR–SSO typing for DR4–Dw subtypes: application to unrelated bone marrow transplant donor selection," *European J Immunogenetics*, 18:97–104 (1991).

(List continued on next page.)

*Primary Examiner*—Robert A. Wax
*Assistant Examiner*—Rebecca Prouty
*Attorney, Agent, or Firm*—Morrison & Foerster

[57] ABSTRACT

A method of human HLA-DR and/or Dw allotype matching comprises:

(i) effecting polymerase chain reaction (PCR) amplification of a HLA-DRB gene exon 2 nucleotide sequence of a first sample of DNA;

(ii) separating according to size the DNA fragments resulting from the said amplification;

(iii) determining the length polymorphism of the thus separated DNA fragments; and (iv) comparing the thus-determined length polymorphism with the length polymorphism of DNA fragments resulting from PCR amplification of the said HLA-DRB gene exon 2 nucleotide sequence of a second sample of DNA.

21 Claims, 7 Drawing Sheets

OTHER PUBLICATIONS

Uryu et al., "A simple and rapid method for HLA–DRB and –DQB typing by digestion of PCR–amplified DNA with allele specific restriction endonucleases," *Tissue Antigens* 35:20–31 (1990).

Bidwell et al., "Human HLA–DR/Dw allotype matching by analysis of HLA–DRB gene PCR product polymorphism (PCR fingerprints)," *Technique* 2:93–100 (1990).

Bohem et al., "HLA–DR beta genes vary in number between different DR specificities, whereas the number of DQ beta genes is constant," *J Immunol 135:2149–2155 (1985)*.

Andersson et al., "Class II Genes of the Human Major Histocompatibility Complex," *J Biol Chem* 262:8748–8758 (1987).

Wood et al., "HLA–DR/Dw matching by PCR fingerprinting: the origin of PCR fingerprints and further applications," *J Immunogenetic* 18:147–153 (1991).

Scharf et al., "Sequence Analysis of the HLA–DRbeta and HLA–DQbeta Loci from Three *Pemphigus vulgaris* Patients," *Human Immunology* 22:61–69 (1988).

Ohmiya et al., Seperation of DNA Fragments by High-–Resolution Ion–Exchange Chromatography on a Nonporous QA Column, *Analytical Biochemistry*, 189:126–130 (1990).

Katz and Dong, "Rapid Analysis and Purification of Polymerase Chain Reaction Products by High–Performance Liquid Chromatography," *Bio Techniques,* 8(5):546–555 (1990)

Bidwell, et al., "Rapid HLA–DR–Dw and DP Matching by PCR Fingerprinting and Related DNA Heteroduplex Technologies," *Handbook of HLA Typing Techniques,* Chapter 3, p. 100–103 (1993), Hui & Bidwell, eds., CRC Press, Boca Raton, Fl.

Clay et al., "PCR–fingerprinting for selection of HLA matched unrelated marrow donors," *Lancet,* 337(8749):1049–1052 (May 4, 1991).

C. M. Nagamine et al., "A PCR Artifact:Geneation of Heteroduplexes" Amer. J. Human Genetics. 45:337–339 (Sep. 1989).

B. L. Triggs–Raine et al., "Diagnostic Heteroduplexes: Simple Detection . . . " Amer. J. Human Genetics 46:183 (Jan. 1990).

D. G. Tenen et al., "Effect of a Stem–Loop Structure within the Su40 . . . " Cell 34:629–639 (Sep. 1983).

Sekiya et al., "An Efficient Method of Detecting Nucleotide Sequence . . . " J. Cell Biochem. 13E:340.

12 # HUMAN LEUKOCYTE ANTIGEN TYPING

This application is a continuation of application Ser. No. 08/116,043, filed Sep. 1, 1993, now abandoned, which is a continuation of Ser. No. 07/652,072, filed on Feb. 6, 1991, now abandoned.

The present invention relates to matching human leukocyte antigens.

The human leukocyte antigen (HLA) class II genes of the human major histocompatibility complex (MHC) encode cell surface glycoproteins with a fundamental role in the immune response: the presentation of antigenic peptides to T helper cells. The recognition by T helper cells of foreign antigen in association with self-MHC class II molecules triggers a cascade of immunological responses resulting in the activation of both cytotoxic T cells and B cells to effect killing of antigen-presenting cells and induction of an antibody response, respectively.

At least six HLA class II loci have been defined, three of which (HLA-DR, DQ and DP) are known to express functional products. Pairs of A (formerly alpha) and B (formerly beta) genes within these three loci encode heterodimeric protein products which are multi-allelic and alloreactive. In addition, combinations of epitopes on DR and/or DQ molecules are recognised by alloreactive T cells. This reactivity has been used to define "Dw" types by cellular assays based upon the mixed lymphocyte reaction (MLR).

As a corollary to DR and DQ alloreactivity, it has been demonstrated that matching of donor and recipient HLA-DR and DQ alleles prior to allogeneic transplantation has an important influence on allograft survival. Therefore, HLA-DR and DQ matching is now generally undertaken as a clinical prerequisite for renal and bone marrow transplantation.

Methods for the identification of alloreactive epitopes have until recently been confined to serological and cellular typing. Serological typing of DR and DQ is well established and employs antisera generated as a result of humoral responses to DR and DQ alloantigens. However, serological typing is frequently problematic, due to the availability and crossreactivity of alloantisera and because live cells are required.

Extensive molecular genetic analysis of the HLA class II region has recently enabled the definition of HLA-DR, DQ and DP alleles at the DNA level. It is now recognised that many polymorphisms detected at the DNA level could not previously be defined serologically. However, the polymorphisms revealed by DNA probes are slowly being confirmed as functional since new alloantisera are being reported which can now define serological "splits". It therefore appears that the polymorphisms detected at the DNA level might well reflect functional epitopes. Therefore, DNA typing is becoming more widely used as an adjunct, or alternative, to serological tests.

To date, the most extensively employed DNA typing method for the identification of these alleles has been restriction fragment length polymorphism (RFLP) analysis. This well established method for HLA class II DNA typing suffers from a number of inherent drawbacks. Thus, RFLP typing is too time-consuming for clinical use prior to cadaveric renal transplantation, and for this reason it is best suited to live donor transplantation or retrospective studies. Furthermore, RFLP does not generally detect polymorphism within the exons which encode functionally significant HLA class II epitopes, but relies upon the strong linkage between allels-specific nucleotide sequences within these exons and restriction endonuclease recognition site distribution within surrounding, generally noncoding, DNA.

The intensive effort by many groups to sequence HLA class II alleles has revealed that the majority of alloreactive epitopes of DRB, DQB, DQA and DPB protein products are confined to the membrane-distal domain, encoded by the second exon of the respective genes. The flanking sequences of these exons are both locus-specific and highly conserved between alleles, and as such they are amenable to enzymatic amplification using the polymerase chain reaction (PCR) technique (Saiki et al, Science 230, 1350, 1985; Scharf et al, Human Immunol. 23, 143, 1988). This technique has expedited the acquisition of nucleotide sequence data for virtually all of the alleles, and in turn has permitted the construction of allele-specific oligonucleotide (ASO) probes which are able to detect allele-specific nucleotide sequence microheterogeneity. As a result, PCR-ASO typing methods have been developed. These rely on the generation by PCR amplification of sufficient target DNA to permit typing by ASO probes using slot- or dot-blot hybridization analysis. Thus, PCR-ASO typing has been used to develop improved procedures for HLA-DR typing, HLA-DQ typing and HLA-DP typing.

The major methodological drawback of these systems is that the complexity of the technique is directly related to the number of alleles under investigation: thus, at least one ASO probe is employed per allele, and therefore one membrane containing immobilized target DNAs is required for each ASO probe used. An alternative strategy has been developed by Scharf et al (1988), whereby immobilized ASO probes are hybridized to enzymatically labelled amplified target DNAs: in this manner, a single membrane containing all of the requisite ASO probes may be used to type each amplified DNA.

We have now devised a new and simple method for HLA-DR/Dw allotype matching which employs PCR amplification of HLA-DRB gene second exon sequences and subsequent product analysis by electrophoretic separation. Rapid separation can be achieved in nondenaturing polyacrylamide minigels. In contrast to currently available DNA typing technology, there are no requirements for post-amplification sample processing such as target DNA denaturation/neutralization, immobilization on solid support membranes, hybridization with radioisotope- or enzyme-labelled ASO probes or development of hybridisation signals.

Accordingly, the present invention provides a method of human HLA-DR and/or Dw allotype matching, which method comprises:

(i) effecting PCR amplification of a HLA-DRB gene exon 2 nucleotide sequence of a first sample of DNA;
(ii) separating according to size the DNA fragments resulting from the said amplification;
(iii) determining the length polymorphism of the thus separated DNA fragments; and
(iv) comparing the thus-determined length polymorphism with the length polymorphism of DNA fragments resulting from PCR amplification of the said HLA-DRB gene exon 2 nucleotide sequence of a second sample of DNA.

The method is founded on PCR amplification of HLA-DRB gene exon 2 sequences with defined PCR primers to generate characteristic allele-specific PCR products (PCR fingerprints). It differs from other established DNA typing methods since there is no requirement for post-amplification enzyme digestion, chemical treatments, DNA immobilization, target-probe hybridizations, or for the use of multiple combinations of PCR oligonucleotide primers. Both HLA-DR and Dw PCR fingerprints can easily be identified in DR/Dw homozygous or heterozygous individuals within 8 hours. Hence, the present method of direct visual comparison between PCR fingerprints of panels of individuals can be adapted for HLA-DR/Dw allotype matching for example in the selection of HLA-DR/Dw-matched living related or unrelated volunteer donors for bone marrow transplantation.

When the DNA of HLA-DR/Dw heterozygous individuals was studied, the observed PCR fingerprints were similar, but not identical, to the patterns expected by the simple addition of two corresponding HLA-DR/Dw homozygous cells. However, if the DNAs from two HLA-DR/Dw homozygous cells are premixed before PCR amplification, the pattern observed in the corresponding heterozygote is reproduced. Therefore the presently described method may be developed for general HLA-DR/Dw allotyping. The DR and/or Dw specificities of heterozygous individuals can therefore be analysed.

The present method is carried out on a first sample of DNA. A sample of DNA is obtained from an individual or any object whose HLA-DR and/or Dw allotypes it is wished to study. Individual includes a foetus. HLA DNA can be extracted from all nucleated cells. Typically, HLA DNA is obtained from peripheral blood cells for convenience. Foetal HLA DNA can be obtained from placental cells or amniotic fluid. Other sources of DNA include hair follicles, mummified bodies, etc.

The DNA is isolated under conditions which preclude degradation. Cells are digested with a protease under such conditions that there is likely to be little or no DNAase activity. The digest is extracted with a DNA solvent. The extracted DNA may be purified by, for example, dialysis or chromatography. Suitable DNA isolation techniques are described by Kan et al in N. Eng. J. Med. 297, 1080–1084, 1977 and Nature 251, 392–393, 1974 and by Kan and Dozy, Proc. Natl. Acad. Sci. USA 75, 5631–5635, 1978.

Exon 2 nucleotide sequences of the HLA-DRB gene of the sample DNA are then amplified by PCR. The flanking sequences of exon 2 are highly conserved between DRB alleles. To the HLA DNA are added two oligonucleotide primers for annealing to complementary sequences at either end of exon 2, a heat-stable DNA polymerass such as TaqI, dATP, dCTP, dGTP and dTTP. The DNA is denatured, the oligonucleotide primers anneal to their complementary sequences with the 3' ends pointing towards each other and the DNA polymerass results in extension of the annealed primers and amplification of the segment of DNA defined by the 5' ends of the primers.

The cycle of DNA denaturation, primer annealing and synthesis of the DNA segment defined by the 5' ends of the primers is repeated as many times as is necessary to amplify the HLA-DRB DNA until sufficient is available for step (ii) of the present method. Amplification may proceed for from 20 to 40 cycles, for example from 25 to 35 cycles.

Any appropriate oligonucleotide primers may be employed. The primers may be suitable for amplification of multiple HLA-DR and/or Dw alleles or for amplification of specific such alleles. Preferred primers for multi-allelic amplification are:

GH46 (left): CCGGATCCTTCGTGTCCCCAGACCACG

GH50 (right): CTCCCCAACCCCGTAGTTGTGTCTGCA

For specific amplification of HLA-DRw8 and -DRw5 (w12), GH50 may be used as the right primer and, for the left primer:

PL8/12: TTCTTGGAGTACTCTACGGG

The primers may be labelled for facilitating analysis in step (iii) of the present method. The primers can be labelled with a directly detectable tag, for example a radionuclide such as $^{32}P$, $^{35}S$, $^{14}C$ or $^{125}I$, a fluorescent compound such as fluorescein or rhodamine derivatives, an enzyme such as a peroxidase or alkaline phosphatase) avidin or biotin. The two primers may have the same or different labels.

The fragments of amplified DNA, i.e. the product of amplification of the exon 2 nucleotide sequence of the HLA-DRB gene of the sample DNA as defined by the PCR primers, are then separated according to size. This may be achieved by electrophoresis or by high pressure liquid chromatography. The separation is effected on a substrate. For electrophoresis, this typically is a gel which does not denature the DNA, such as polyacrylamide gel.

The amplified DNA is separated on the gel according to the size of each fragment. Electrophoresis is conducted under conditions which effect a desired degree of resolution of fragments. A degree of resolution that separates fragments that differ in size by as little as about 10 bp is usually sufficient. Size markers may also be run on the gel to permit estimation of the size of fragments.

The size distribution, i.e. the resolution pattern, of the amplified DNA fragments will be allele-specific. This resolution pattern or PCR fingerprint can next be visualised. Where a PCR primer has been labelled, this label may be revealed. A substrate carrying the separated labelled DNA fragments is contacted with a reagent which detects the presence of the label. Where the PCR primers were not labelled, the substrate bearing the PCR fingerprint may be contacted with ethidium bromide and the DNA fragments visualised under ultraviolet light.

The length polymorphism of the DNA fragments is thus determined. This is compared with the length polymorphism of DNA fragments resulting from PCR amplification of the HLA-DRB exon 2 nucleotide sequence of a second sample of DNA. In this way, correspondence between the HLA-DR and/or Dw allotypes of the DNA samples may be obtained.: It may be ascertained whether the length polymorphism of the DNA fragments obtained, and therefore whether the allotypes of the two samples are the same or not. If the allotype of the second DNA sample is known, the allotype of the first DNA sample may be identified if the allotypes are the same.

The length polymorphism in respect of the second sample of DNA may be obtained using the same conditions as are employed to obtain the length polymorphism in respect of the first DNA sample. Typically the same primers are used. PCR amplification need not necessarily be for the same number of cycles or under identical reaction conditions, though. Similarly, separation of the resulting DNA fragments need not be carried out in an identical fashion provided it is possible to assess the relative correspondence of the length polymorphisms of the DNA fragments resulting from amplification of each DNA sample.

The second sample of DNA may be analysed according to the present method simultaneously with or at a different time to analysis of the first DNA sample. Indeed, a multiplicity of DNA samples may be analysed. Typically the or each sample is a selected sample. Samples from selected individuals can be analysed. The length polymorphism determined for each sample may be held in a computer.

A computer database may therefore be generated containing the size distribution patterns for different samples, for different DR and/or Dw specificities or, indeed, for all DR and Dw specificities. The different molecular sizes of the PCR generated fragments for samples and/or for the different DR and/or Dw specificities determined for known samples could be keyed into a computer. Any unknown DR and/or Dw types could therefore be determined ("typed") by comparing the sizes of the fragments generated after PCR of DNA of the unknown sample with the reference database. In step (iv) of the present method, therefore, the length polymorphism in respect of the first sample of DNA may be compared with a length polymorphism held on a computer database in respect of a second sample of DNA.

The PCR fingerprint may be compared with another PCR fingerprint to determine whether the individuals, whose DNA has been tested to obtain the two fingerprints, have matching HLA-DR and Dw allotypes. The present method can therefore be applied to DNA samples from two or more individuals. Alternatively, a PCR fingerprint may be compared with a standard fingerprint previously obtained. Correspondence between fingerprints can therefore be determined.

The present method can be used to determine whether a donor of a transplant or transfusion and a receipient or proposed recipient of the transplant or transfusion have matching HLA-DR and Dw allotypes. PCR fingerprints from the donor and the recipient or proposed recipient can be compared. The transplant may be a tissue transplant such as a heart, lung, liver or kidney transplant or a bone marrow transplant. The transfusion may be a blood transfusion. HLA-DR/Dw matching of living related or unrelated donors for allogenic transplantation may therefore be achieved.

Alternatively, the present method can be used in determining paternity of an individual. By comparing PCR fingerprints obtained for the individual, the individual's mother and the suspected father of the individual, this determination can be made. Also, the present method can be used in determining whether an individual is susceptible to or has a disease associated with HLA-DR and/or Dw allotypes. Such diseases are reviewed in Immunol. Rev. 70, 1–218, 1983.

The invention also provides a test kit, which kit comprises:
(a) two oligonucleotide primers suitable for use in PCR and capable of annealing to complementary sequences at respective ends of exon 2 of a HLA-DRB gens; and
(b) a control DNA and/or control PCR amplification product.

The primers may be labelled as above. The control DNA and control PCR amplification products are also typically labelled. The kit may further comprise one or more of the following:
a heat-stable DNA polymerass such as TaqI;
dATP, dCTP, dGTP and dTTP; and
a database comprising the length polymorphisms of DNA fragments generated by PCR amplification of selected DNA samples.

The length polymorphisms stored in the data base may be those of DNA samples of known DR and/or Dw specificity. The database may therefore comprise the PCR fingerprints for known DR and/or Dw allotypes, indeed for all such allotypes available. The length polymorphisms as reported in FIGS. 2, 3 and 5 for DR or Dw allotypes or as reported in FIG. 4 for the possible combinations of these allotypes may therefore be provided in the database.

The following Example illustrates the invention. In the accompanying drawings:

FIG. 1 shows sample temperature during PCR amplification. One PCR cycle is shown. The durations of cycle segments (a) to (f) are detailed in the Example.

Figure 2:
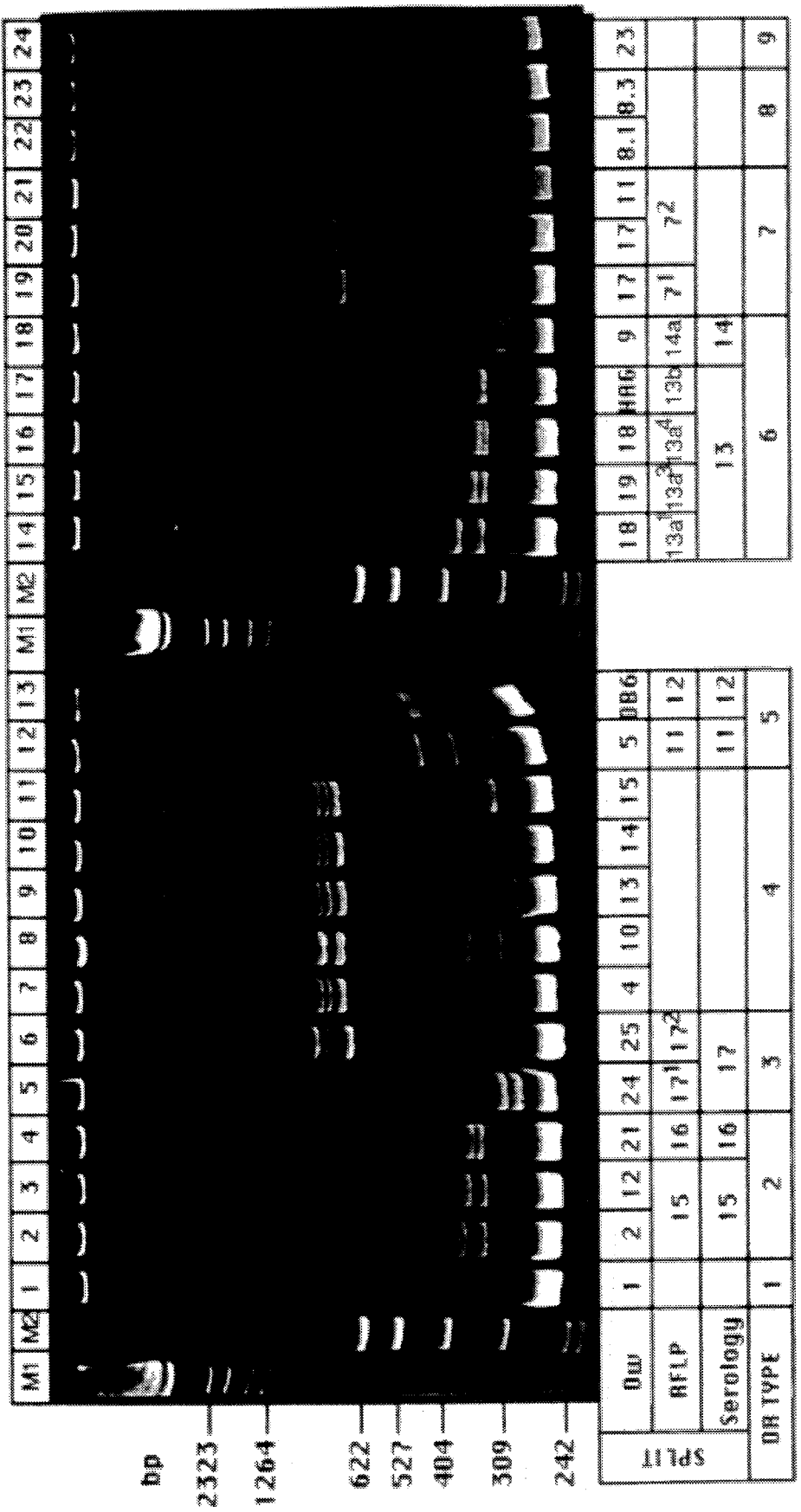

FIG. 2 shows PCR fingerprints of HLA-DR/Dw homozygous B-lymphoblastoid cell lines (BLCLs). HLA-DRB gene exon 2 sequences were amplified using GH46 plus GH50 PCR primers. M1 and M2, molecular size markers (M1, BstEII digest of bacteriophage lambda; M2, MspI digest of pBR322. Molecular size shown in base pairs (bp)). Cells shown are: Lane 1, BAF (ECACC 87033001); Lane 2, CI (9w0201); Lane 3, BGE (9w1201); Lane 4, RML (10w9016); Lane 5, CAA-0 (ECACC 85051626); Lane 6, QBL (ECACC 85022807); Lane 7, BOB-2; Lane 8, TS-10 (9w1005); Lane 9, SSTO (9w1303); Lane 10, LS-40 (9w1403); Lane 11, HAS-15 (9w9902); Lane 12, RAG; Lane 13, J-SIM (T29639: from E. Bidwell); Lane 14, HBS (9w0601); Lane 15, EMJ (9w0606); Lane 16, JTED (9w0603); Lane 17, HAG (9w1802); Lane 18, BRU (9w0901); Lane 19, PIT (9w0704); Lane 20, BH13 (9w1901); Lane 21, KIJ (9w1104); Lane 22, BAE (9w0807); Lane 23, LUY (9w0805); Lane 24, DKB (9w and 10w: Ninth and Tenth International Histocompatibility Workshop reference numbers; ECACC: European Collection of Animal Cell Cultures reference number). The HLA-DR and Dw allotypes are shown: workshop (w) prefixes have been omitted for the sake of clarity. Where appropriate, RFLP-defined splits are also shown.

Figure 3:
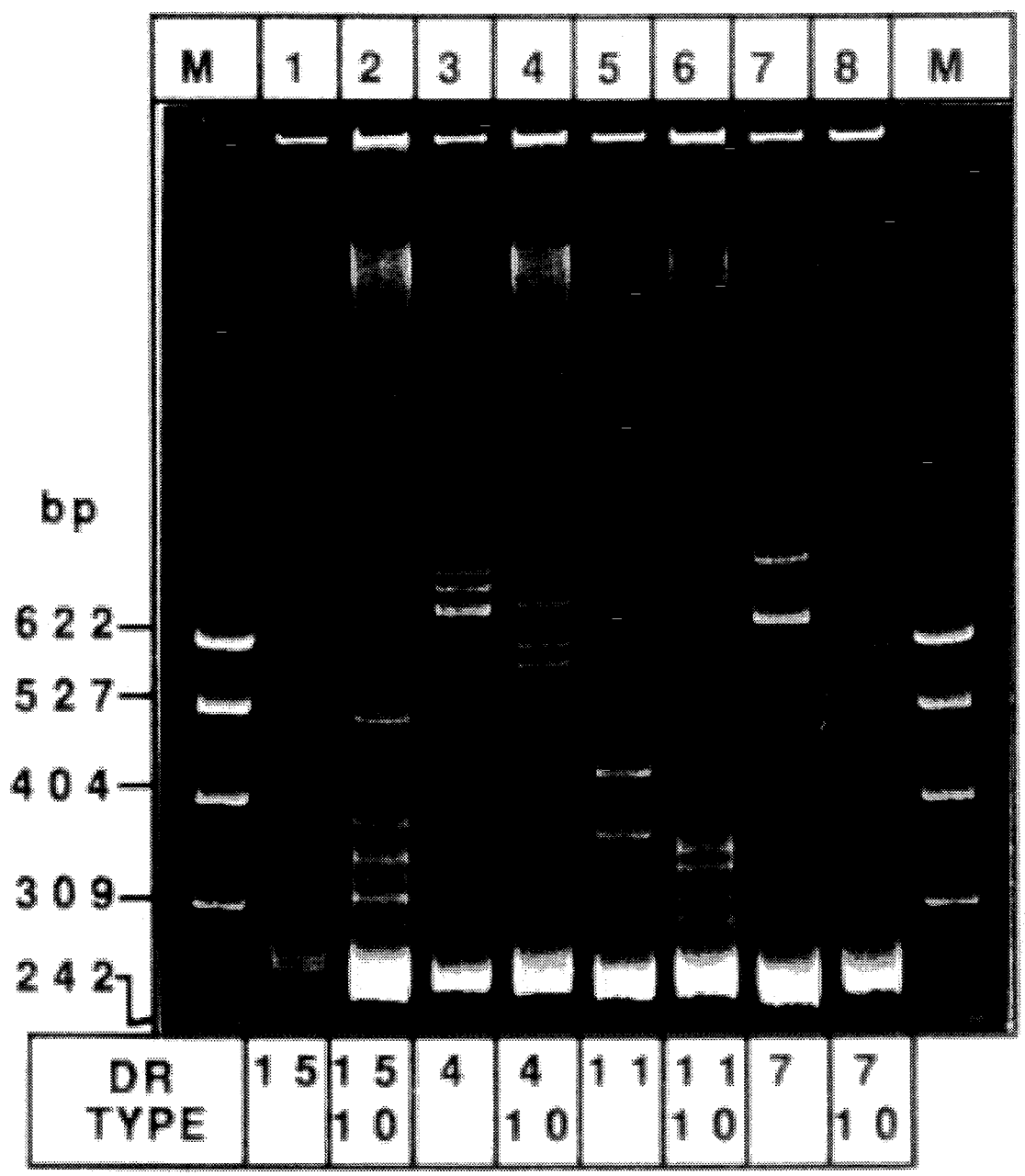

FIG. 3 shows PCR fingerprints of HLA-DRw10-positive heterozygous cells. Cells shown are: Lane 1, CI (9w0201); Lane 2, C164; Lane 3, BOB-2; Lane 4, C1103; Lane 5, KRO (9w0905); Lane 6, R287; Lane 7, BUP (9w0702); Lane 8, R295. The DR serologic specificities are shown. M, molecular size markers (MspI digest of pBR322). Primers used and abbreviations as for FIG. 2.

Figure 4:
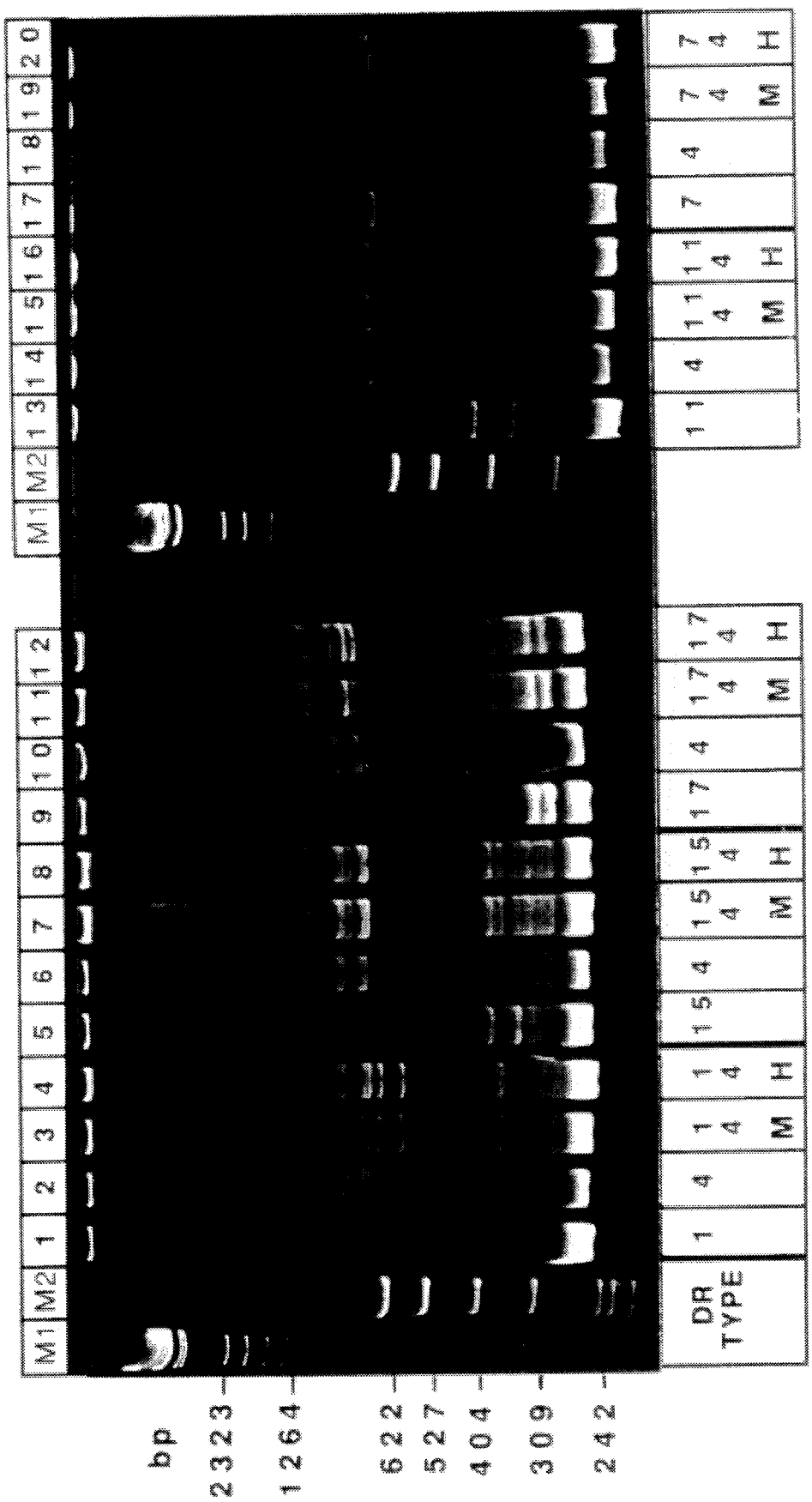

FIG. 4 shows PCR fingerprints of HLA-DR/Dw heterozygous cells. For each of the five groups of cells shown, PCR fingerprints of homozygous and heterozygous cells are compared. M, DNAs from two homozygous cells (0.5 µg of each DNA) mixed before PCR amplification. H, DNA from HLA-DR/Dw heterozygous individuals. Cells shown are:. Lane 1, AL (9w0101); Lane 2, BOB-2; Lane 3, AL plus BOB-2; Lane 4, C84; Lane 5, CI (9w0201); Lane 6, BOB-2; Lane 7, CI plus BOB-2; Lane 8, C650; Lane 9; CAA-0 (ECACC 85051626); Lane 10, BOB-2; Lane 11, CAA-0 plus BOB-2; Lane 12, C508; Lane 13, KRO (9w0505); Lane 14, BOB-2; Lane 15, KRO plus BOB-2; Lane 16, C595; Lane 17, BUP (9w0702); Lane 18, BOB-2; Lane 19, BUP plus BOB-2; Lane 20, C667. The HLA-DR serologic specificities are shown. Primers used and molecular size markers M1 and M2 as for FIG. 2.

Figure 5:
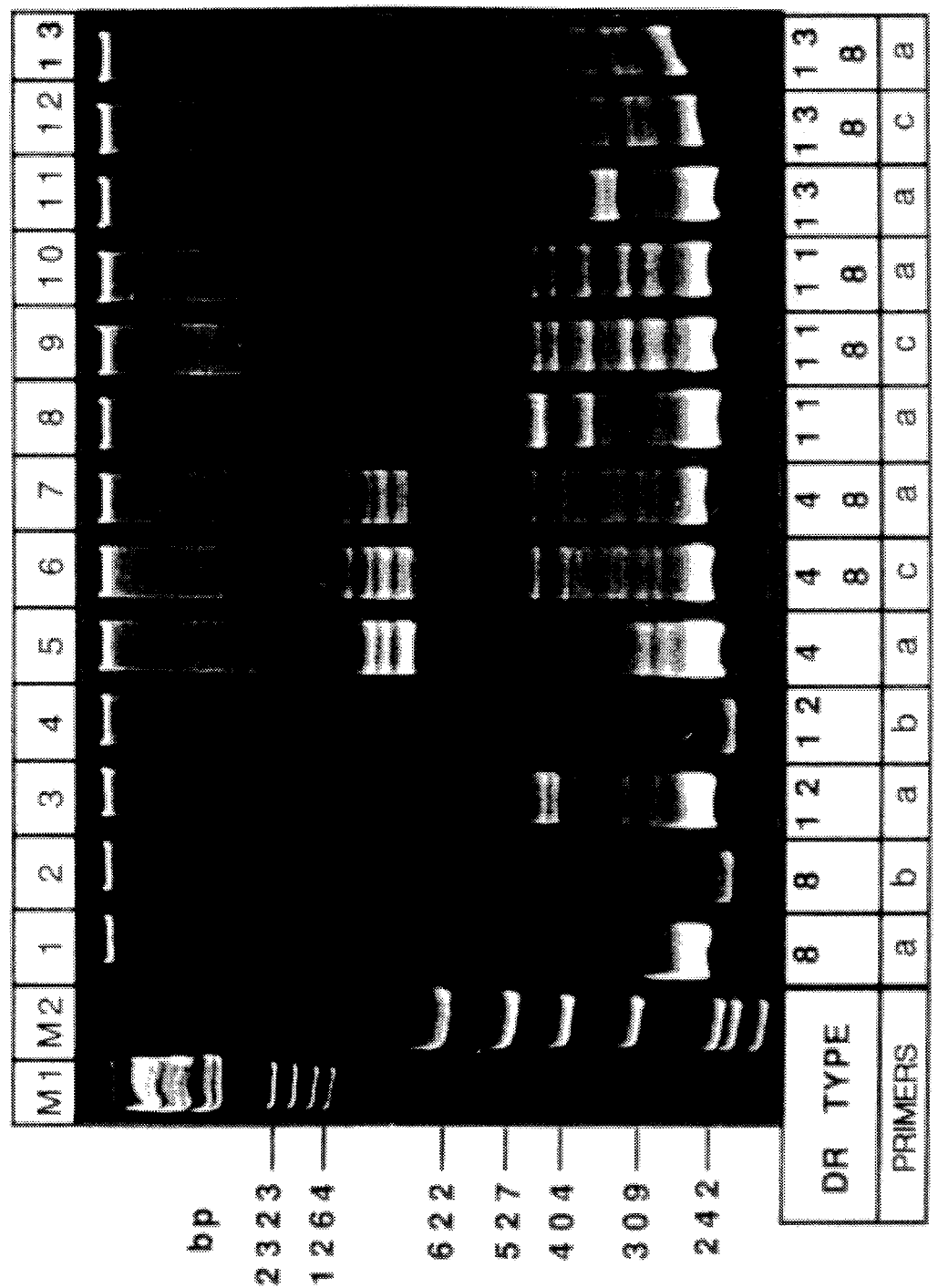

FIG. 5 shows PCR fingerprints of HLA-DRwS-positive cells. Combinations of PCR primers used were: a, GH46 plus GH50; b, PLS/12 plus GH50; c, GH46 plus PL8/12 plus GH50. Allele-specific amplification of DRw8 and DRw12 is shown (lanes 2 and 4 respectively): no amplification of other DR haplotypes was observed (not shown). Cells shown are: Lanes 1 and 2, BAE (9w0807); Lanes 3 and 4, J-SIM (T29639); Lane 5, BOB-2; Lanes 6 and 7, C810; Lane 8, RAG; Lanes 9 and 10, C246; Lane 11, JTED (9w0603); Lanes 12 and 13, C372. The HLA-DR serologic specificities are shown. Molecular size markers M1 and M2 as for FIG. 2.

Figure 6:
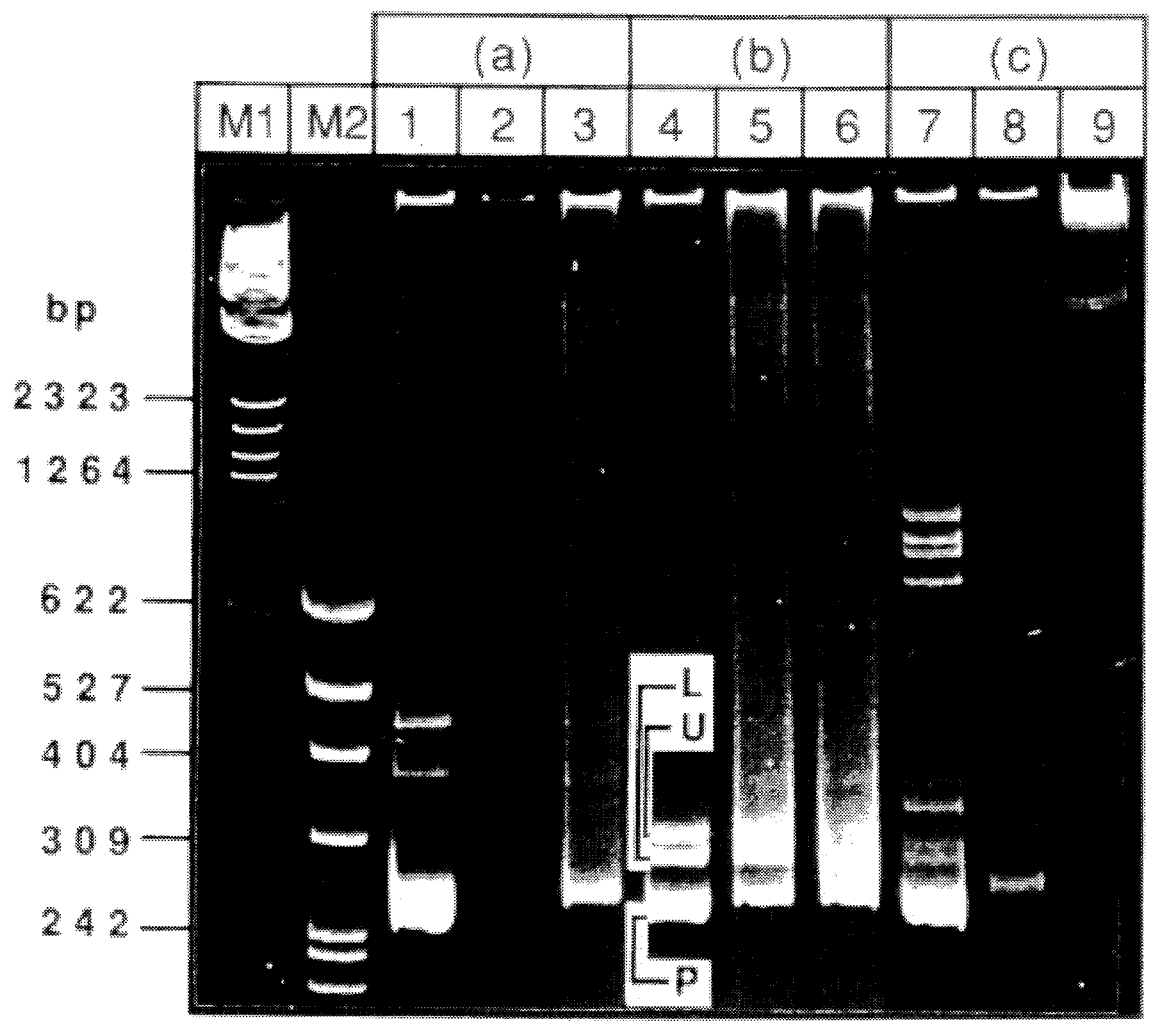

FIG. 6 shows the results of regeneration of primary PCR product from satellite DNA sequences. (a) Reamplification of primary PCR product: Lane 1, genomic DNA from the DR1-homozygous BLCL, BAF (ECACC 87033001) amplified with GH46 plus GH50 primers; Lanes 2 and 3, purified primary (271 bp) product from lane 1, reamplified without primers (lane 2) and with GH46 plus GH50 primers (lane 3). (b) Reamplification of satellite DNA sequences: Lane 4, genomic DNA from the DR3(w17)-homozygous BLCL, CAA-0 (ECACC 85051626) amplified with GH46 plus GH50 primers showing primary (271 bp) product (P) and upper (U) and lower (L) satellite DNA sequences; Lanes 5 and 6, purified U and L satellite DNA, respectively, reamplified with GH46 plus. GH50 primers. (c) Satellite DNA sequences are not generated from HLA-DRB cDNA: Lane 7, genomic DNA from the HLA-DR9-homozygous BLCL, DKB, amplified with GH46 plus GH50 primers; Lane 8, plasmid DNA (2µg) from a DR9 DRB cDNA clone amplified with GH46 plus GH50 primers; Lane 9, as lane 8 but not amplified. Molecular size markers M1 and M2 as for FIG. 2.

Figure 7:
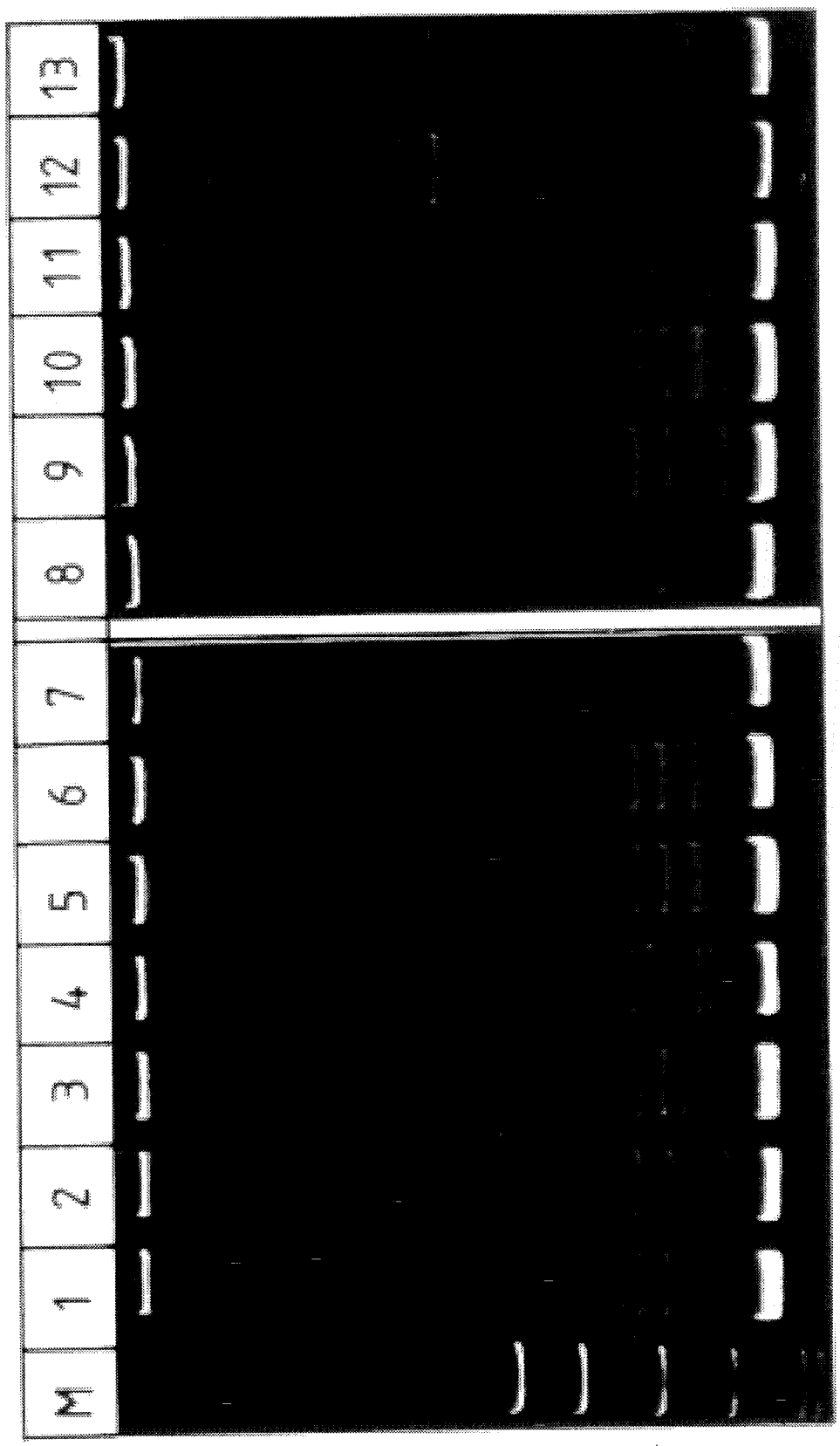

FIG. 7 shows the PCR fingerprints of Example 2

EXAMPLE 1

MATERIALS AND METHODS

Cells

Well characterized BLCLs, homozygous for DLA-Dr/Dw alleles, were obtained from originating laboratories participating in the Ninth and Tenth International Histocompatibility Workshops: or where appropriate, from the European Collection of Animal Cell Cultures, Porton Down, GB. HLA-DR/Dw heterozygous cells were characterized by, and obtained from, Mars. E. Bidwell (United Kingdom Transplant Service, Bristol, GB). HLA-DR and Dw allotypes were confirmed by RFLP typing of TaqI-digested genomic DNA, using short DRB, DQB and DQA cDNA probes, as previously described (Bidwell, Immunol. Today 9, 18–23, 1988; Bidwell et el, Transplantation 45, 640–646, 1988).

PCR Amplification

Reaction mixtures (100 µl) contained 1µg (for BLCLs) or 2µg (for HLA-DR/Dw heterozygous cells) of genomic DNA, prepared as described (Bidwell et al, 1988), 10 mM Tris-HCl, pH 8.3, 1.5 mM MgCl2, 0.01% (w/v) gelatin, 0.2 mM each of dATP, dCTP, dGTP and dTTP, and 1 µM each of MLA-DRB gone second exon 5' (left) and 3' (right) oligonucleotide primers. The primers used were (a) for multi-allelic amplification, GH46 (left, nucleotide sequence 5'CCGGATCCTTCGTGTCCCCAGACCACG3') (Scharf et al, Human. Immunol. 22, 61–69, 1988) plus GH50 (right, nucleotide sequence 5'CTCCCCAACCCCGTAGTTGT-GTCTGCA3') (Scharf et al, Human Immunol. 22, 61–69, 1988); (b) for specific amplification of HLA-DRw8 and DRw5(w12), PLS/12 (left, nucleotide sequence 5'TTCTTG-GAGTACTCTACGGG3') plus GH50 (right). For combined amplification, 1 µM each of GH46, PL8/12 and GH50 were used. Mixtures were heated at 94° C. for 5 mins, placed on ice for 2 mins, and 2.5 units of Taq polymerase (Perkin Elmer Cetus, Norwalk, Conn.06859, U.S.A.) were added. DNA amplification was performed using a programmable cyclic reactor (Ericomp Inc., San Diego, Calif.92121, U.S.A.). Amplification cycle parameters were: 60 secs at 94° C (FIG. 1(d)), 90 secs cooling ramp (FIG. 1(e)), 120 secs at 65° C. (FIG. 1(f)), 70 secs heating ramp (FIG. 1(a)), 120 secs at 72° C. (FIG. 1(b)) and 160 secs heating ramp (FIG. 1(c)). After 35 cycles of amplification, the 72° C. heating step was extended by 10 mins.

Polyacrylamide Gel Electrophoresis

Aliquots of PCR-amplified DNA (10 µl) were subjected to electrophoresis for 95 min at 200 volts in nondenaturing polyacrylamide minigels (12% w/v acylamide: N,N'-bisacrylamide (29:1), in 1 ×TBE (89 mM Tris-borate, 89 mM boric acid, 2 mM EDTA pH 8.0)) using a proprietary vertical minigel electrophoresis system (Bio-Rad Laboratories, Richmond, Calif.94804, U.S.A.). The dimensions of the formed gel were 82 mm(w)×72 mm(h)×0.75 mm(d), containing 15 sample slots of dimensions 3 mm(w)×10 mm(h)× 0.75 mm(d). After electrohoresis, gels were immersed for 30 mins in 1 ×TBE containing ethidium bromide (0.5 µg/ml) and DNA was visualized using a 302 nm ultraviolet transilluminator. For reamplification experiments, DNA was excised from the polyacrylamide gels and purified by isotachophoresis and ethanol precipitation. Aliquots were reamplified using the same conditions described above.

RESULTS

PCR Fingerprints of HLA-DR/Dw Homozygous Cells

To establish an easy and reproducible molecular method for the determination of HLA-DR and Dw allotypes, we employed the PCR amplification technique to amplify allele-specific sequences. When the HLA-DRB gene exon 2-specific GH46 and GH50 primers were used to amplify DNA from a series of HLA-DR/Dw homozygous BLCLs, allele-specific patterns of polymorphic PCR products (PCR fingerprints) could be established that were associated with individual HLA-DR. serotypes (FIG. 2). Moreover, splits of HLA-DR specificities defined by both alloreactive T cells (Dw allotypes) and by DNA-RFLP typing produced further allele-specific PCR fingerprints. For each HLA-DR/Dw specificity, groups of phenotypically identical BLCLs were examined: each group revealed identical PCR fingerprints (not shown). The PCR fingerprints consisted of a primary product (271 bp as predicted from a series of HLA-DRB gens exon 2 nucleotide sequences) together with multiple higher molecular weight products (hereafter designated satellite DNAs). With the exception of HLA-DRw8 homozygous BLCLs (see below), allele-specific multiple satellite DNAs ranging from 290 bp to 1000 bp were observed. One cluster of satellite DNAs (650 bp–1000 bp) appeared to correlate with the supertypic HLA-Drw53 serologic specificity, associated with HLA-DR4, DR7 and DR9 (FIG. 2, lanes 7–11, 19–21 and 24).

PCR Fingerprints of HLA-DR/Dw Heterozygous Cells

Experiments were conducted to compare the PCR fingerprints of HLA-DR/Dw homozygous and heterozygous cells. These revealed that the PCR fingerprints of HLA-DR/Dw heterozygous cells could not be entirely predicted from the simple summation of patterns observed in the corresponding HLA-DR/Dw homozygous cells (FIGS. 4 and 5). However, the PCR fingerprints of the former were exactly reproducible by premixing DNAs from the corresponding HLA-DR/Dw homozygous cells before PCR amplificiation. FIG. 4 shows five such representative experiments. Premixing DNAs thus=permits the construction of predetermined combinations of HLA-DR/Dw specificities for use as reference DNAs.

Since no HLA-DRw10 homozygous cells have been described, we examined this specificity by analysis of PCR fingerprints of HLA-DR210 heterozygous individuals. In each case studied, unique PCR fingerprints were observed, though no consensus HLA-DRw10-specific satellite DNA band was observed (FIG. 3).

The PCR fingerprints of HLA-DRw8 homozygous BLCLs revealed a primary (271bp) product, but no detectable satellite DNAs (FIG. 2, lanes 22 and 23) and thus represented a potential difficulty in identification of the HLA-DRw8 allele in HLA-DR/Dw heterozygous individuals. We therefore constructed a 5' (left) PCR primer for the purpose of allele-specific amplification. This primer, PLS/12 (see Materials and Methods) is complementary only to HLA-DRw8 and DRw5(w12) DRB1 gene exon 2 5'-sequences. We confirmed the specificity of PLS/12 on an extended panel (not shown) of HLA-DR/Dw homozygous and heterozygous cells: both HLA-DRw8 and DR25(w12)-positive cells revealed a primary amplification product of 242bp as predicted from the primer annealing location (FIG. 5, lanes 2 and 4). However, neither the inclusion nor the omission of the PLS/12 primer from PCR amplification with GH46 plus GH50 primers affected resulting PCR fingerprints. These revealed, as for all other HLA-DR/Dw heterozygous cells examined, unique additional satellite DNA bands not observed in the relevant homozygous cells (FIG. 5, lanes 5–13). This permitted the identification of the HLA-DRw8 specificity in HLA-Dr/Dw heterozygotes without recourse to allele-specific PCR primers.

Regeneration of Primary PCR Products from Purified Satellite

DNA Sequences

To investigate the possible origin of the satellite DNA sequences observed, primary (271 bp) product bands and satellite DNA bands were excised from polyacrylamide gels, purified, and reamplified as described above.

Reamplification of the primary product band from the HLA-DR1 homozygous cell line BAF failed to regenerate the satellite DNA sequences observed after amplification of genomic DNA (FIG. 6(a)), indicating that these satellites do not arise from HLA-DRB gene exon 2 sequences in isolation from flanking DNA. Reamplification of purified satellite DNA bands from the HLA-DR3(w17) homozygous cell line CAA-O showed that, for each band reamplified, the lower molecular weight bands observed in genomic DNA PCR fingerprints were regenerated. Thus, primary product (P) and lower satellite (L) bands were regenerated from the upper satellite (U) band; and the P band was regenerated from the L band (FIG. 6(b)). This further indicates that satellite DNA bands might consist of a nested set of sequences, each containing part or all of the P sequence.

To test whether satellite DNA sequences could be generated from a full length HLA-DRB gene cDNA clone, amplification products of genomic DNA and cDNA from DR9 haplotypes were compared. Only the P sequence was generated from the cDNA clone (FIG. 6(c)), indicating again that specific flanking sequences may be required to generate satellite DNAs.

The Origin of PCR Fingerprints

PCR fingerprints consist of a principal (leading) DNA band and a series of satellite (trailing) DNA bands. The principal band represents homoduplexed MLA-DRB gens second exon PCR products. The number of individual homoduplexes present in this band corresponds to the number of different DRB genes which contain amplifiable second exon sequences and which are present on both haplotypes of an individual. Satellite DNA bands are heteroduplexes formed by heterologous association of different HLA-DRB gens products during the last annealing stage of the PCR. These heteroduplexes contain variable regions of nucleotide sequence mismatches, depending upon the combination of DRB alleles within both haplotypes. Regions of mismatch confer on such heteroduplexes a molecular conformation different from the progenitor homoduplexes. This permits the resolution of homoduplexes and heteroduplexes by nondenaturing polyacrylamide gel electrophoresis. The extent of nucleotide sequence mismatches between alleles is haplotype specific: thus, the number and gel mobilities of heteroduplexes is haplotype specific. This permits the discrimination between haplotypes using PCR fingerprinting. For HLA-DR/Dw heterozygotes, additional heteroduplexes are observed when compared to the superimposed PCR fingerprints of the corresponding homozygous typing cells, since trans association generates new heteroduplex conformations.

DNA Crossmatching Technique

This technique was developed as a further application of PCR fingerprinting. It permits (a) resolution between similar PCR fingerprints shown by cells of different HLA-DR/Dw allotypes, and (b) the assignment of HLA-DR/Dw allotypes.

1. Resolution between Similar PCR Fingerprints

Cells of different HLA-DR/Dw allotypes may occasionally demonstrate similar PCR fingerprints. Identity or difference in allotype may be confirmed by DNA crossmatching, defined as:
(1) the mixing equivalent amounts of genomic DNAs from the two cells prior to PCR amplification, or (2) mixing equivalent amounts of postamplification PCR products, denaturing the mixture, for example at 94° C. for 1 minute, allowing reannealing to occur by incubation, for example at 65° C. (2 minutes), and subsequent primer extension, for example at 72° C. (9 minutes). Matching of HLA-DR/Dw allotypes of the cells is indicated when no difference is observed between PCR fingerprints derived from individual cell DNAs and from the mixture. Difference between HLA-DR/Dw allotypes of the cells is indicated when one or more new DNA satellite bands (heteroduplexes), not present in PCR fingerprints of either of the individual cell DNAs, are observed in the PCR fingerprint of the mixture of cell DNAs (the DNA crossmatch).

2. Assignment of HLA-DR/Dw Allotypes

Assignment of HLA-DR/Dw allotypes may be achieved by a series of DNA crossmatches, between a Test DNA of unknown HLA-DR/Dw type, and a panel of homozygous typing cells (HTCs) of known individual HTC DNA/Test DNA crossmatch and that of the Test DNA ("a negative DNA crossmatch") indicates that the Test DNA contains the haplotype represented by the HTC DNA. Disparity of PCR fingerprints between an individual HTC DNA/Test DNA crossmatch and that of the Test DNA (a "positive DNA crossmatch") indicates that the Test DNA does not contain the haplotype represented by the HTC DNA. An HLA-DR/Dw heterozygous Test DNA will give negative DNA crossmatches with two different HTC DNAs.

3. HLA-DR/Dw Crossmatching Kit

An HLA-DR/Dw Crossmatching Kit comprises (1) an oligonucleotide primer set for amplifying HLA-DRB gene second exon sequences: (2) buffers for the polymerase chain reaction (PCR) amplification and for gel loading; and (3) a set of genomic DNAs from a set of characterised HLA-DR/Dw homozygous typing cells. Instructions for performing genomic DNA isolation, purification and assay, PCR amplification, DNA crossmatching, and analysis of results, are also typically provided. DNA crossmatching permits the typing of HLA-DR/Dw allotypes by simple visual comparison of PCR fingerprints created either by (1) the mixed amplification of test DNA with a panel of separate homozygous typing cell (HTC) DNAs, or by (2) post PCR-amplification mixing of test and HTC PCR products, followed by denaturation and reannealing.

PCR fingerprints. Thus in FIG. 7a, spiking of DR2(w15)-Dw2 and DRw6(w13)-Dw18 genomic DNAs with DRw8 genomic DNA before amplification gave rise to new and easily distinguishable PCR fingerprints (lanes 3 and 4, respectively). This technique may also be applied with equal effect (not shown) by mixing respective PCR products after amplification, denaturing, and allowing mixtures to reanneal.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCGGATCCTT CGTGTCCCCA GACCACG 27

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CTCCCCAACC CCGTAGTTGT GTCTGCA 27

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TTCTTGGAGT ACTCTACGGG 20

EXAMPLE 2

Although PCR fingerprints appear to be unique for each combination of DR haplotypes so far examined, those from certain unrelated DR haplotypes may demonstrate marked similarities. For example, the PCR fingerprints of HLA DR2(w15)-Dw2 and DRw6(W13)-Dw18 homozygous cells are very similar (FIG. 7a, lanes 1 and 2 respectively). In order to easily discriminate between such specificities, we devised experimental spiking of PCR mixtures before amplification with genomic DNA from a DRw8-homozygous typing cell. Since the DRw8 haplotype contains only one amplifiable DRB gene second exon, which differs in sequence from all other alleles, mixed amplification of genomic DNA from a DRw8-homozygous cell with that from other DR specificities resulted in the formation of new heteroduplexes. The conformations of these new heteroduplexes allowed discrimination between otherwise similar

We claim:

1. A method of human HLA-DR and/or Dw allotype matching, which method, consists initially of the following steps:

(i) effecting polymerase chain reaction (PCR) amplification of a HLA-DRB gene exon 2 nucleotide sequence of a first sample of DNA;

(ii) separating the DNA fragments resulting from said amplification by non-denaturing polyacrylamide gel electrophoresis;

(iii) observing the positions on the non-denaturing polyacrylamide gel of the thus separated DNA fragments to determine a PCR fingerprint; and (iv) comparing the thus-determined fingerprint with the fingerprint resulting from PCR amplification of the said HLA-DRB gene exon 2 nucleotide sequence of a second sample of DNA.

2. A method according to claim 1, wherein step (i) is effected with two oligonucleotide primers each carrying a radionuclide, fluorescent, enzyme, avidin or biotin label.

3. A method according to claim 1, wherein two oligonucleotide primers having the following nucleotide sequences are employed in step (i);

CCGGATCCTTCGTGTCCCCAGACCACG (SEQ. ID NO.: 1); and CTCCCCAACCCCGTAGTTGTGTCTGCA (SEQ. ID NO.: 2).

4. A method according to claim 2, wherein two oligonucleotide primers having the following nucleotide sequences are employed in step (i);

CCGGATCCTTCGTGTCCCCAGACCACG ( SEQ. ID NO.: 1 ); and CTCCCCAACCCCGTAGTTGTGTCTGCA (SEQ. ID NO.: 2).

5. A method according to claim 1, wherein PCR amplification is effected in step (i) for from 25 to 35 cycles.

6. A method according to claim 2, wherein PCR amplification is effected in step (i) for from 25 to 35 cycles.

7. A method according to claim 3, wherein PCR amplification is effected in step (i) for from 25 to 35 cycles.

8. A method according to claim 4, wherein PCR amplification is effected in step (i) for from 25 to 35 cycles.

9. A method according to claim 1, wherein steps (i) to (iii) are carried out on a sample of DNA from a donor of a transplant or transfusion and a sample of DNA from a recipient or proposed recipient of the transplant or transfusion and the thus-determined fingerprints are compared in step (iv) to ascertain whether the donor and recipient have matching HLA-DR and Dw allotypes.

10. A method according to claim 2, wherein steps (i) to (iii) are carried out on a sample of DNA from a donor of a transplant or transfusion and a sample of DNA from a recipient or proposed recipient of the transplant or transfusion and the thus-determined fingerprints are compared in step (iv) to ascertain whether the donor and recipient have matching HLA-DR and Dw allotypes.

11. A method according to claim 3, wherein steps (i) to (iii) are carried out on a sample of DNA from a donor of a transplant or transfusion and a sample of DNA from a recipient or proposed recipient of the transplant or transfusion and the thus-determined fingerprints are compared in step (iv) to ascertain whether the donor and recipient have matching HLA-DR and Dw allotypes.

12. A method according to claim 5, wherein steps (i) to (iii) are carried out on a sample of DNA from a donor of a transplant or transfusion and a sample of DNA from a recipient or proposed recipient of the transplant or transfusion and the thus-determined fingerprints polymorphisms are compared in step (iv) to ascertain whether the donor and recipient have matching HLA-DR and Dw allotypes.

13. A method according to claim 4, wherein steps (i) to (iii) are carried out on a sample of DNA from a donor of a transplant or transfusion and a sample of DNA from a recipient or proposed recipient of the transplant or transfusion and the thus-determined fingerprints are compared in step (iv) to ascertain whether the donor and recipient have matching HLA-DR and Dw allotypes.

14. A method according to claim 6, wherein steps (i) to (iii) are carried out on a sample of DNA from a donor of a transplant or transfusion and a sample of DNA from a recipient or proposed recipient of the transplant or transfusion and the thus-determined fingerprints are compared in step (iv) to ascertain whether the donor and recipient have matching HLA-DR and Dw allotypes.

15. A method according to claim 7, wherein steps (i) to (iii) are carried out on a sample of DNA from a donor of a transplant or transfusion and a sample of DNA from a recipient or proposed recipient of the transplant or transfusion and the thus-determined fingerprints are compared in step (iv) to ascertain whether the donor and recipient have matching HLA-DR and Dw allotypes.

16. A method according to claim 8, wherein steps (i) to (iii) are carried out on a sample of DNA from a donor of a transplant or transfusion and a sample of DNA from a recipient or proposed recipient of the transplant or transfusion and the thus-determined fingerprints are compared in step (iv) to ascertain whether the donor and recipient have matching HLA-DR and Dw allotypes.

17. A test kit suitable for use in a method of human HLA-Dr and/or Dw allotype matching as defined in claims 1, which kit comprises:

(a) two oligonucleotide primers capable of annealing to complementary sequences at respective ends of exon 2 of a HLA-DR gene;

(b) a set of genomic DNAs and/or PCR amplification products from a set of characterized HLA-DR/Dw homozygous typing cells; and (c) data comprising the PCR fingerprints for known HLA-DR and/or Dw allotypes.

18. A kit according to claim 17, wherein the primers each carry a radionuclide, fluorescent, enzyme, avidin or biotin label.

19. A kit according to claim 17, which further comprises a heat-stable DNA polymerase and/or dATP, dCTP, dGTP and dTTP.

20. A kit according to claim 18, which further comprises a heat-stable DNA polymerase and/or dATP, dCTP, dGTP and dTTP.

21. A kit according to claim 17, comprising:

(1) an oligonucleotide primer set for amplifying HLA-DRB gene second exon sequences;

(2) buffers for PCR amplification and for gel loading; and (3) a set of genomic DNAs from a set of characterised HLA-DR/Dw homozygous typing cells.

* * * * *